US00PP30623P3

(12) United States Plant Patent
Miller

(10) Patent No.: US PP30,623 P3
(45) Date of Patent: Jun. 25, 2019

(54) ***SALVIA* PLANT NAMED 'ROSEBURG'**

(50) Latin Name: *Salvia microphylla*
Varietal Denomination: Roseburg

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 19 days.

(21) Appl. No.: 15/731,610

(22) Filed: Jul. 8, 2017

(65) Prior Publication Data

US 2019/0014710 P1 Jan. 10, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Anne Marie Grunberg
(74) *Attorney, Agent, or Firm* — Cassandra Bright

(57) ABSTRACT

A new and distinct cultivar of *Salvia* plant named 'Roseburg' is disclosed, characterized by flowers which are typically bicolored red/magenta and white, that can become solid red/magenta in cool temperatures. Plants over-winter well and have a good response to pruning back. Branches are flexible and resist breakage. The new variety is a *Salvia microphylla*, normally produced as an outdoor garden or container plant.

2 Drawing Sheets

Figure 1:
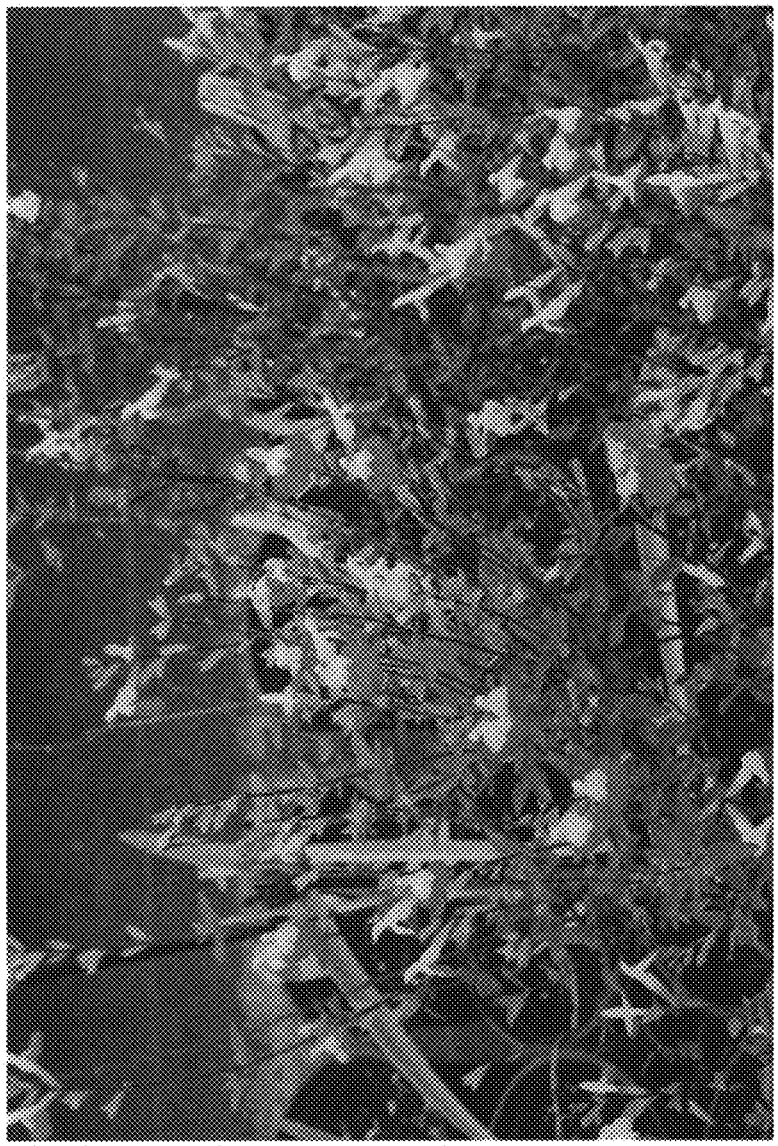

Latin name of the genus and species: *Salvia microphylla*. Variety denomination: 'Roseburg'.

BACKGROUND OF THE INVENTION

The new *Salvia* cultivar is a product of a planned breeding program conducted by the inventor, Luen Miller, in Royal Oaks, Calif. The objective of the breeding program was to produce new *Salvia* varieties with denser plant habits, strong garden performance, in a range of flower colors. The open pollination resulting in this new variety was made during Summer of 2009.

The seed parent is the unpatented, *Salvia microphylla* 'Hot Lips'. The pollen parent is unknown as it was an open pollination breeding program. The new variety was identified as a potentially interesting selection in June 2010, at a commercial nursery in Royal Oaks, Calif.

Asexual reproduction of the new cultivar 'Roseburg' by terminal vegetative cuttings was first performed during June of 2010, at a commercial nursery in Royal Oaks, Calif. Subsequent propagation has shown that the unique features of this cultivar are stable and reproduced true to type on successive generations.

SUMMARY OF THE INVENTION

The cultivar 'Roseburg' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Roseburg' These characteristics in combination distinguish 'Roseburg' as a new and distinct *Salvia* cultivar:

1. Deep magenta/red and white bicolor flower during warm temperatures, turning solid magenta/red during cool conditions.
2. Glossy foliage.
3. Excellent branch resilience and resistance to breakage.
4. Good overwintering performance, responds well to pruning back.

PARENT COMPARISON

Plants of the new cultivar 'Roseburg' are similar to plants of the seed parent in most horticultural characteristics, however, plants of the new cultivar 'Roseburg' differ in the following:

1. Flowers of the new variety have a magenta/red coloration. The parent variety has orange/red and white bicolor flowers.
2. Flowers of the new variety can become a solid color in cool temperatures, flowers of the seed parent are always bicolor.
3. Plants of the new variety are less upright in habit.
4. Plants of the new variety have smaller, deeper green leaves than the parent variety.

COMMERCIAL COMPARISON

Plants of the new cultivar 'Roseburg' can also be compared to the commercial variety *Salvia greggii* 'Furman's Red', unpatented. These varieties are similar in most horticultural characteristics; however 'Roseburg' differs in the following:

1. Plants of the new variety begin blooming approximately 4 to 8 weeks earlier than this comparator.
2. Flowers of the new variety are typically bicolor, unless temperatures turn cool, flowers of this comparator are typically solid colored.

3. The new variety produces glossier, darker leaves than this comparator.
4. Plants of the new variety are denser than plants of this comparator.

Plants of the new cultivar 'Roseburg' can also be compared to the commercial variety *Salvia* 'BALMIRCHER', U.S. Plant Pat. No. 28,527. These varieties are similar in most horticultural characteristics; however 'Roseburg' differs in the following:

1. Plants of the new variety are larger and more vigorous than this comparator.
2. Flowers of the new variety are typically bicolor, unless temperatures turn cool, flowers of this comparator are typically solid colored.
3. The new variety produces glossier leaves than this comparator.

BRIEF DESCRIPTION OF THE PHOTOGRAPHS

The accompanying photograph in FIG. 1 illustrates in full color typical plants of 'Roseburg' grown in a nursery, in Royal Oaks, Calif., in commercial 1 quarter containers. FIG. 1 illustrates the 'Roseburg' variety of plant grown in one gallon pots.

Figure 2:
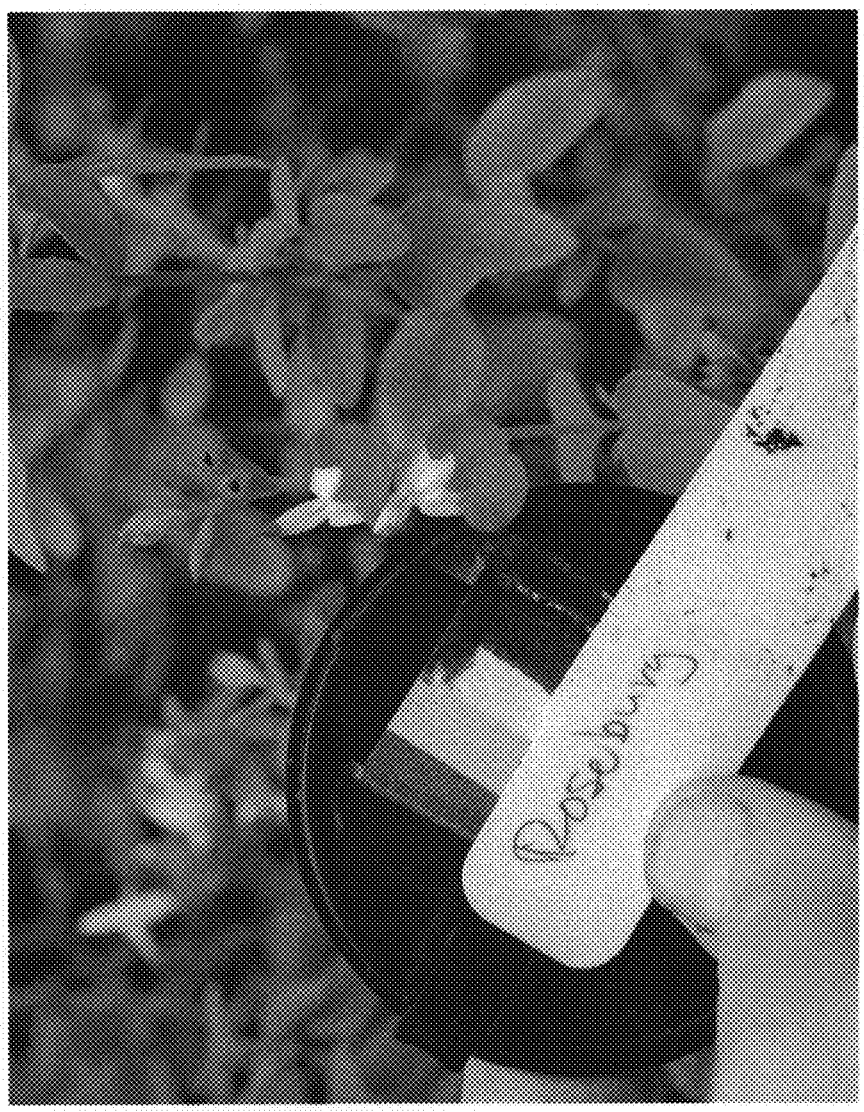

FIG. 2 illustrates in full color typical flowers of 'Roseburg'. Age of the plants photographed are approximately 26 weeks from unrooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Roseburg' plants grown in a nursery in Royal Oaks, Calif. The growing temperature ranged from approximately 10° C. to 30° C. The nursery is un-shaded, giving bright, normal sunlight conditions. Measurements and numerical values represent averages of typical plant types. Botanical classification: *Salvia microphylla* 'Roseburg'.

PROPAGATION

Root description: Fine, densely fibrous. Colors include Green-White 157D on new growth and Orange-White 159C, Grey-Brown 199B and 199C for older roots.

PLANT

Growth habit: Upright and somewhat outwardly angled.

Height: Approximately 45 cm to top of foliage. Approximately 60 cm to top of flowering plane. Measured from soil level of pot.

Plant spread: Approximately 80 cm.

Growth rate: Rapid.

Branching characteristics: Very well branched. Approximately 4 to 6 branches emerging from a pinch, which branch into another 5 to 7 primary lateral branches.

Length of primary lateral branches: Approximately 12 to 28 cm.

Diameter of lateral branches: Approximately 0.35 cm.

Quantity of lateral branches: About 20 to 38.

Stem:

*Color*.—RHS Yellow-Green 144B, striped Greyed-Purple 187A.

*Texture*.—Slightly hirsute and strongly ribbed. Older growth scaly.

Internode length: Average range 3.5 to 4.5 cm.

Age of plant described: Approximately 1.5 years.

FOLIAGE

Leaf:

*Arrangement*.—Opposite.

*Quantity*.—Average range 16 to 24 fully expanded and immature leaves per main branch with side branches.

*Average length*.—Approximately 1.9 cm. including petiole.

*Average width*.—Approximately 1.0 cm.

*Shape of blade*.—Ovate to nearly deltoid.

*Apex*.—Acute.

*Base*.—Broad attenuate, nearly truncate.

*Attachment*.—Stalked.

*Margin*.—Crenate.

*Texture of top surface*.—Glossy, glabrous. Finely reticulated.

*Texture of bottom surface*.—Glossy, glabrous. Prominent reticulated veins.

*Color*.—Young foliage upper side: Near RHS Green 137B. Young foliage under side: Near RHS Green 137C. Mature foliage upper side: Near RHS Green 137A. Mature foliage under side: Near RHS Green 138B.

*Venation*.—Type: Reticulate. Venation color upper side: Near RHS Green 138B. Venation color under side: Near RHS Green 138B.

*Petiole*.—Average Length: Approximately 0.3 cm. Diameter: Approximately 0.1 cm. Color: Near Yellow-Green 144A.

*Other*.—Foliage strongly aromatic.

FLOWER

Natural flowering season: Flowering from early Spring through late Summer.

Inflorescence type and habit: Flowers arranged in verticillasters on spikes.

Flower longevity on plant: Individual flowers last approximately 7 to 10 days on the plant. Each spike lasts approximately 6 to 8 weeks with flowers. Corolla self-cleaning, calyx persistent.

Quantity of flowers: About 6 to 10 buds and 10 to 16 fully opened flowers per spike, at one time. Mature plants have approximately 80 to 120 spikes.

Spike size:

*Diameter*.—Approximately 3.5 cm.

*Height*.—Approximately 7.0 to 13.0 cm.

Individual flowers:

Size:

*Diameter*.—Approximately 1.6 cm.

*Length*.—Approximately 2.5 cm.

*Fragrance*.—Moderately, slightly sweet aromatic scent.

Corolla:

*Petal arrangement*.—The corolla is sympetalous and typically bilabiate with 2 small, fully fused lobes forming a single upper lip and 3 larger fused lobes forming a lower lip.

*Margin*.—Entire.
*Tip shape*.—Upper lip tip obtuse, lower lip tip retuse.
*Length*.—Upper lip Approximately 1.1 cm. Lower lip Approximately 1.3 cm. Tube length Approximately 1.5 cm.
*Width*.—Upper lip: Approximately 0.4 cm, lower lip Approximately 1.5 cm. Tube width: Approximately 0.6 cm.
*Texture*.—Upper lip: Glabrous interior, pubescent exterior. Sticky. Lower lip: Glabrous all surfaces.

Color:
*Upper lip*.—When opening: Inner surface: Near RHS White N155D, apex Red-Purple 61C. Outer surface: Near RHS White N155D, apex Red-Purple 61A. Fully opened: Inner surface: Near RHS White N155D, apex Red-Purple 63C. Outer surface: Near RHS White N155D, apex Red-Purple 61A. Fading: Inner surface: Near RHS White N155D, apex Red-Purple 63C. Outer surface: Near RHS White N155D, apex Red-Purple 61A.

Color:
*Lower lip*.—When opening: Inner surface: Between RHS Red 53A and Red-Purple N66A. Faint basal blotch near White N155B. Outer surface: Near RHS Red-Purple 61B. Fully opened: Inner surface: Between RHS Red 53A and Red-Purple N66A. Prominent basal blotch near White N155D. Outer surface: Near RHS Red-Purple 61B. Fading: Inner surface: Near RHS Red-Purple 60B. White basal blotch disappears, or faintly White N155D. Outer surface: Near RHS Red-Purple 60B.

Color:
*Tube*.—When opening: Inner surface: Near RHS White N155D streaked Red-Purple 60D. Outer surface: Near RHS Red-Purple 61A streaked White N155D. Fully opened: Inner surface: Near RHS White N155D streaked Red-Purple 60D. Outer surface: Near RHS Red-Purple 61A streaked White N155D. Fading: Inner surface: Near RHS Red-Purple 72B, faintly streaked Red-Purple 69B. Outer surface: Near RHS Red-Purple 71A, faintly streaked Red-Purple 69D.

Bud: Flower bud includes immature calyx which completely surrounds immature corolla.
*Shape*.—Ovoid.
*Length*.—Approximately 1.4 cm.
*Diameter*.—Approximately 0.4 cm.
*Color*.—Near RHS Red-Purple 71A, large blotches near White N155D.

Calyx:
*Length*.—Approximately 1.1 cm.
*Diameter*.—Approximately 0.4 cm.
*Shape*.—Tubular.

Sepals:
*Shape*.—Quantity per flower: 3, fused to form a tube. Unfused apex.
*Length*.—Approximately 0.3 cm unfused portion.
*Width*.—Approximately 0.4 cm.
*Margin*.—Entire.
*Apex*.—Short apiculate.
*Texture*.—Slightly hirsute and ridged.
*Color*.—Immature: Near Yellow-Green 144C, well defined stripes near Greyed-Purple N187A. Mature: Near Yellow-Green 144C, well defined stripes near Greyed-Purple N187A.

Peduncle:
*Length*.—Average 2.5 cm.
*Diameter*.—0.3 cm.
*Color*.—Near RHS Yellow-Green 144C, lightly flushed Greyed-Purple N186B.
*Orientation*.—Straight or very slightly curved. Occurring at approximately 15 degree angle from center of plant.
*Strength*.—Moderately strong.
*Texture*.—Slightly hirsute, ridged.

Pedicels:
*Length*.—Average 0.3 cm.
*Diameter*.—0.1 cm.
*Color*.—Near RHS Greyed-Purple N186B.
*Orientation*.—Straight, approximately 15 degree angle from attachment.
*Strength*.—Strong.
*Texture*.—Hirsute.

REPRODUCTIVE ORGANS

Stamens:
*Number*.—2.
*Filament length*.—Approximately 0.5 cm.
*Filament color*.—Near RHS White N155B, flushed Red-Purple N66B.

Anthers:
*Shape*.—Linear.
*Length*.—0.1 cm.
*Color*.—Near RHS Red-Purple 59A.
*Pollen*.—Moderate pollen observed, colored near RHS Yellow-Orange 20A.

Pistil:
*Number*.—1.
*Length*.—Approximately 2.7 cm.
*Style*.—Length: Approximately 2.2 cm. Color: Near RHS White N155D, flushed Red-Purple 64C.
*Stigma*.—Shape: Forked. Color: Near RHS Red-Purple 61A. Ovary: Colored near RHS Yellow-Green 145D, oblong, approximately 0.2 cm long and 0.1 in diameter.

OTHER CHARACTERISTICS

Seeds and fruits: Moderate seed production. One or two seeds mature per flower. Oblong, approximately 4 mm long, 2 mm wide. Colored near Brown 200A.

Disease/pest resistance: Neither resistance nor susceptibility to pathogens and pests common to *Salvia microphylla* have been observed.

Temperature tolerance: The new variety tolerates temperatures within USDA zones 3 to 8.

What is claimed is:

1. A new and distinct cultivar of *Salvia* plant named 'ROSEBURG' as herein illustrated and described.

* * * * *